(12) United States Patent
Flaherty et al.

(10) Patent No.: US 7,220,387 B2
(45) Date of Patent: May 22, 2007

(54) DISPOSABLE SENSOR FOR USE IN MEASURING AN ANALYTE IN A GASEOUS SAMPLE

(75) Inventors: Bryan Flaherty, Half Moon Bay, CA (US); Bhairavi Parikh, Palo Alto, CA (US); Kevin Nason, Menlo Park, CA (US); David Chazan, Palo Alto, CA (US); Johnathan Fay, San Mateo, CA (US); John Kaiser, Menlo Park, CA (US); James Stone, Saratoga, CA (US)

(73) Assignee: Apieron Biosystems Corp., Palo Alto, CA (US)

( * ) Notice: Subject to any disclaimer, the term of this patent is extended or adjusted under 35 U.S.C. 154(b) by 255 days.

(21) Appl. No.: 10/767,709

(22) Filed: Jan. 28, 2004

(65) Prior Publication Data

US 2005/0083527 A1    Apr. 21, 2005

Related U.S. Application Data

(63) Continuation-in-part of application No. 10/334,625, filed on Dec. 30, 2002, now abandoned.

(60) Provisional application No. 60/398,216, filed on Jul. 23, 2002.

(51) Int. Cl.
    *G01J 1/50*     (2006.01)
    *G01N 33/497*   (2006.01)
(52) U.S. Cl. .................. 422/86; 356/433; 356/437
(58) Field of Classification Search ........ 356/433–435, 356/437; 422/84–86
    See application file for complete search history.

(56) References Cited

U.S. PATENT DOCUMENTS

| 3,792,272 | A |   | 2/1974  | Harte et al. |
|-----------|---|---|---------|--------------|
| 3,948,345 | A |   | 4/1976  | Rosencwaig |
| 4,370,553 | A |   | 1/1983  | Waycaster et al. |
| 3,792,272 | A |   | 7/1986  | Harte et al. |
| 5,317,156 | A |   | 5/1994  | Cooper et al. |
| 5,831,742 | A | * | 11/1998 | Watson et al. .............. 356/434 |
| 5,922,610 | A |   | 7/1999  | Alving et al. |
| 6,033,368 | A | * | 3/2000  | Gaston et al. ................ 422/84 |
| 6,076,392 | A |   | 6/2000  | Drzewiecki |
| 6,095,986 | A |   | 8/2000  | Braig et al. |
| 6,186,958 | B1 |  | 2/2001  | Katzman et al. |
| 6,363,772 | B1 |  | 4/2002  | Berry |
| 6,419,634 | B1 |  | 7/2002  | Gaston, IV et al. |
| 6,479,019 | B1 |  | 11/2002 | Goldstein et al. |
| 6,491,643 | B2 |  | 12/2002 | Katzman et al. |
| 6,599,253 | B1 |  | 7/2003  | Baum et al. |
| 6,632,402 | B2 |  | 10/2003 | Blazewicz et al. |
| 6,635,415 | B1 | * | 10/2003 | Bollinger et al. ............. 422/82 |
| 6,656,127 | B1 |  | 12/2003 | Ben-Oren et al. |
| 2001/0021815 | A1 | | 9/2001 | Katzman et al. |
| 2003/0105407 | A1 | | 6/2003 | Pearce, Jr. et al. |
| 2003/0208131 | A1 | | 11/2003 | George |

* cited by examiner

OTHER PUBLICATIONS

Aylott et al., "Optical Biosensing of Gaseous Nitric Oxide Using Spin-Coated Sol-Gel Thin Films" Chemical Materials, 1997, 9, 2261-2263.*

*Primary Examiner*—Richard A. Rosenberger
(74) *Attorney, Agent, or Firm*—Townsend and Townsend and Crew LLP.; M. Henry Heines

(57) ABSTRACT

The present invention is a disposable sensor for use with a device that quantifies analytes in a gaseous sample. It comprises (i) a sensing element, (ii) a means for interfacing the disposable sensor with a gas analysis device, and (iii) a housing. When used with a device that can quantify the concentration of an analyte in a gas sample, the present invention facilitates the use of exhaled breath analysis as a clinical tool.

14 Claims, 7 Drawing Sheets

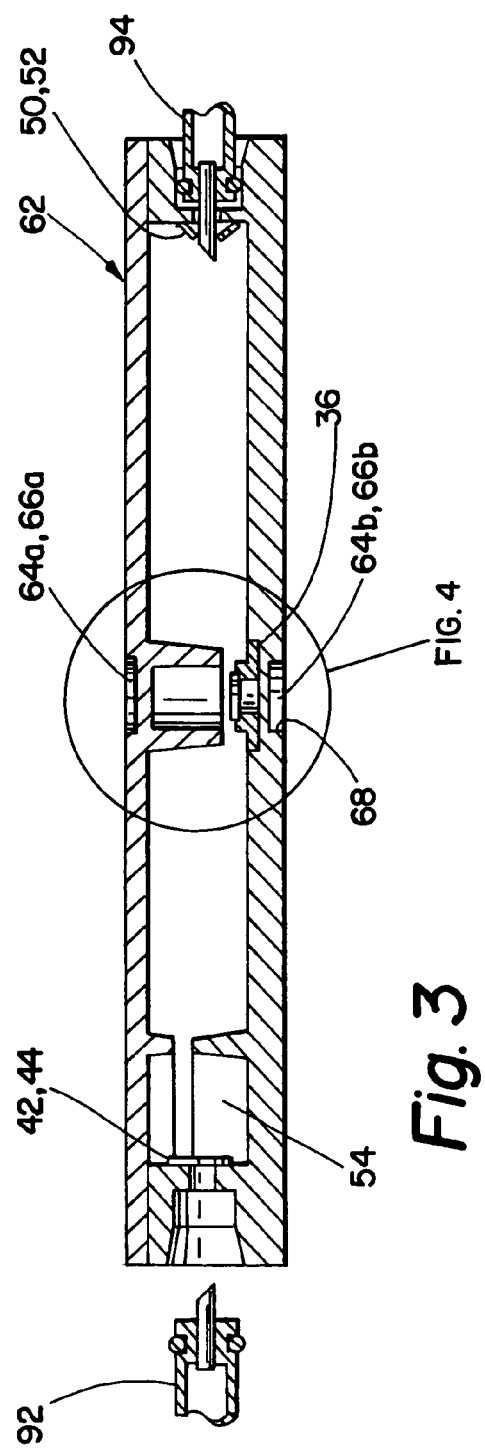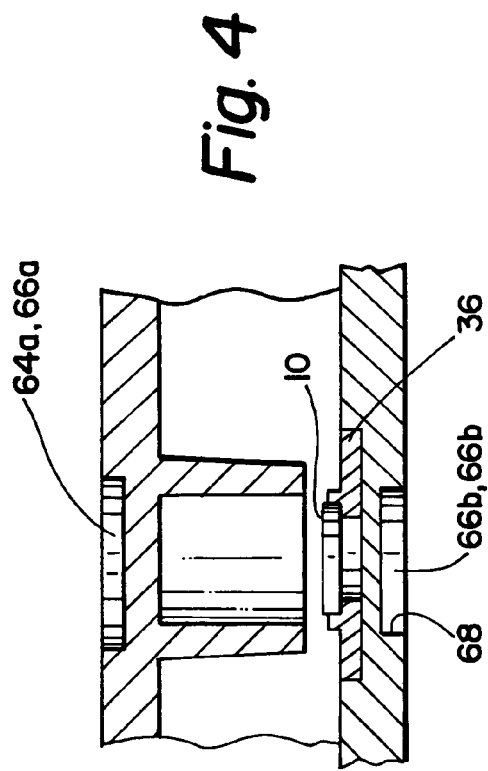

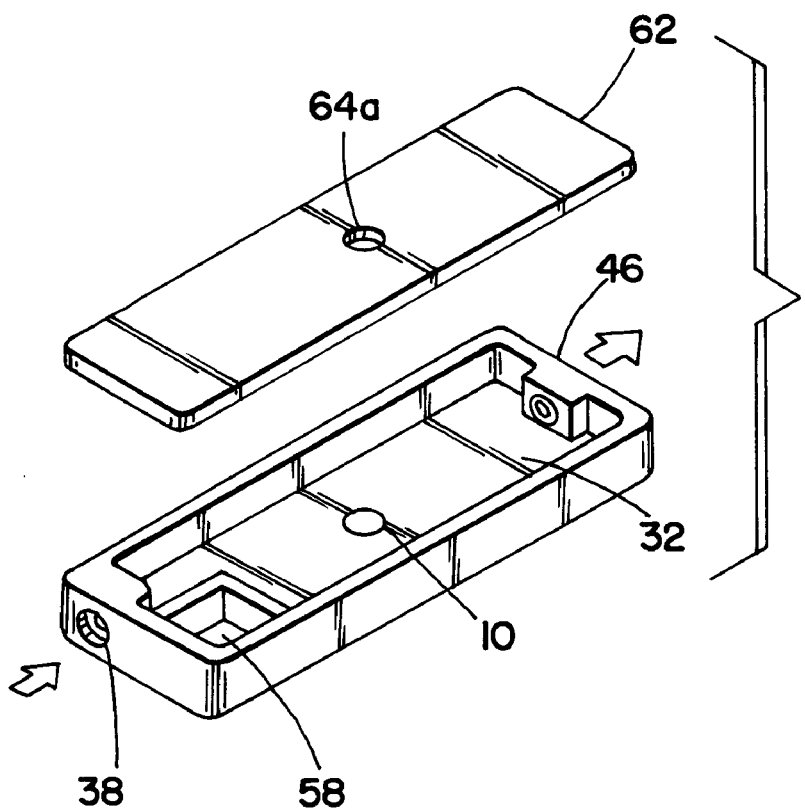
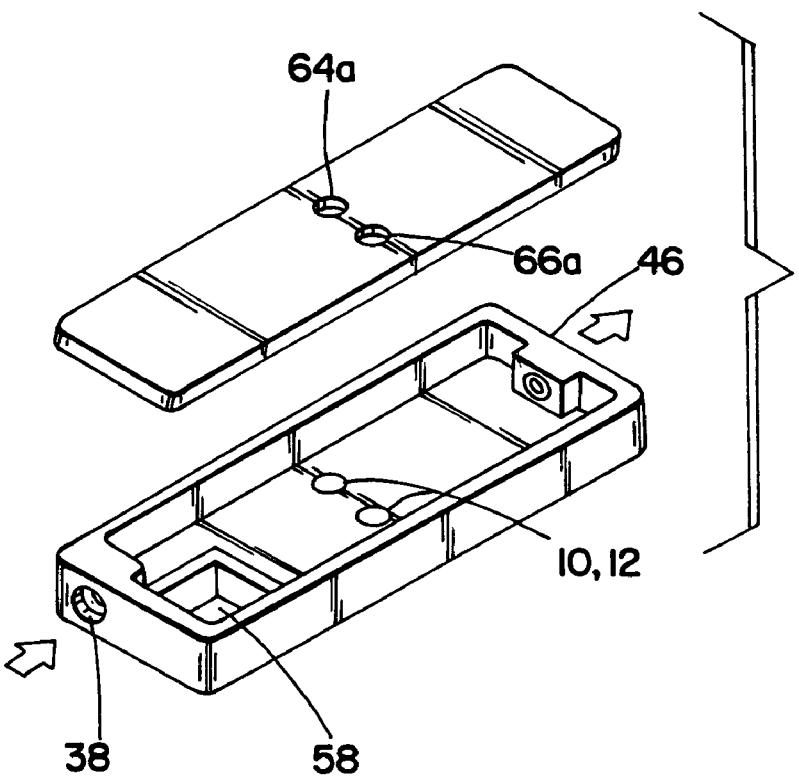

DISPOSABLE SENSOR FOR USE IN MEASURING AN ANALYTE IN A GASEOUS SAMPLE

RELATED APPLICATIONS

This application is a continuation in part of the non-provisional application filed on Dec. 30, 2002, (U.S. Ser. No. 10/334,625), now abandoned, which in turn claims the benefit of the provisional application filed on Jul. 23, 2002 (U.S. Ser. No. 60/398,216).

BACKGROUND OF THE INVENTION

1. Field of the Invention

This invention relates to sensors for use in measuring an analyte or analytes in a gaseous sample.

2. General Background

Analysis of a subject's exhaled breath is a promising clinical tool, with potential application in the diagnosis and treatment of many conditions. For instance, changes in nitric oxide (NO) concentration in exhaled breath can indicate a change in the level of inflammation in the airway of an asthmatic, indicating an increase in the likelihood of an asthmatic attack. Excessive carbon monoxide (CO) can indicate hemolytic jaundice, and high levels of hydrogen can indicate carbohydrate malabsorption. Additionally, breath analysis can be used by law enforcement officials and others to test for the concentration of alcohol in a subject's breath.

It would be especially desirable if patients could conduct their own breath analysis, at home, work, or school. If they could do so, breath analysis could be used to manage chronic diseases such as asthma. Indeed, some of the present inventors have developed both a device (U.S. Ser. No. 10/334,625) for quantifying breath analytes, and a method for managing asthma by monitoring NO levels (U.S. Ser. No. 10/659,408). The disclosures of these applications are incorporated herein by reference as if set out in full.

A necessary part of any portable breath analysis system is the sensor that responds in some way to the analyte in the subject's breath. For a variety of reasons, sensors that are appropriate for a portable system are not re-usable or may require calibration or user intervention to function adequately. There are a variety of large laboratory-based instruments available, but they are generally cumbersome, expensive and difficult to maintain. Therefore, there is a need for a true disposable or calibration-free multi-use system.

SUMMARY OF THE INVENTION

The present invention is a disposable sensor for use with a device that quantifies analytes in a gaseous sample. It comprises (i) a sensing element, (ii) a means for interfacing the disposable sensor with a gas analysis device, and (iii) a housing surrounding said sensing element. The housing need not be a disposable component, but could be integrated into the reusable portion of the system.

BRIEF DESCRIPTION OF THE DRAWINGS

FIG. 3 is a cross-sectional view of a disposable sensor according to an embodiment of the present invention, showing the sensor as it is being attached to gas analysis device.

FIG. 4 is a close-up of the circled area on FIG. 3.

FIG. 6 is an exploded perspective view of a disposable sensor according to an embodiment of the present invention, in which the sensor has only a single sensing element and a single cell.

FIG. 7 is an exploded perspective view of a disposable sensor according to an embodiment of the present invention, in which the sensor has two sensing elements and a single cell.

DETAILED DESCRIPTION

Figure 1:
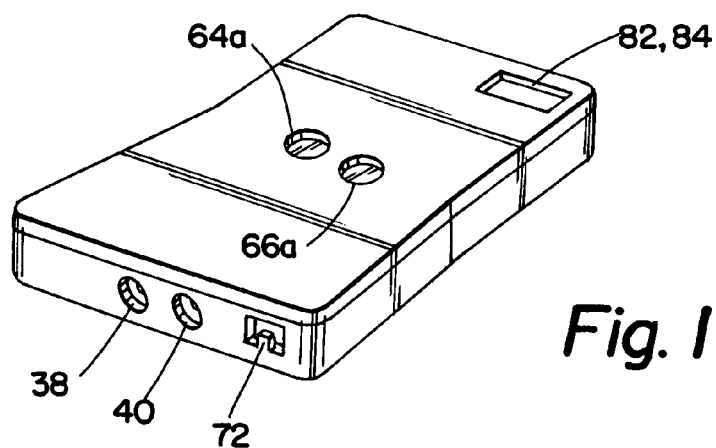
FIG. 1 is a perspective view of a disposable sensor according to an embodiment of the present invention.
Figure 2:
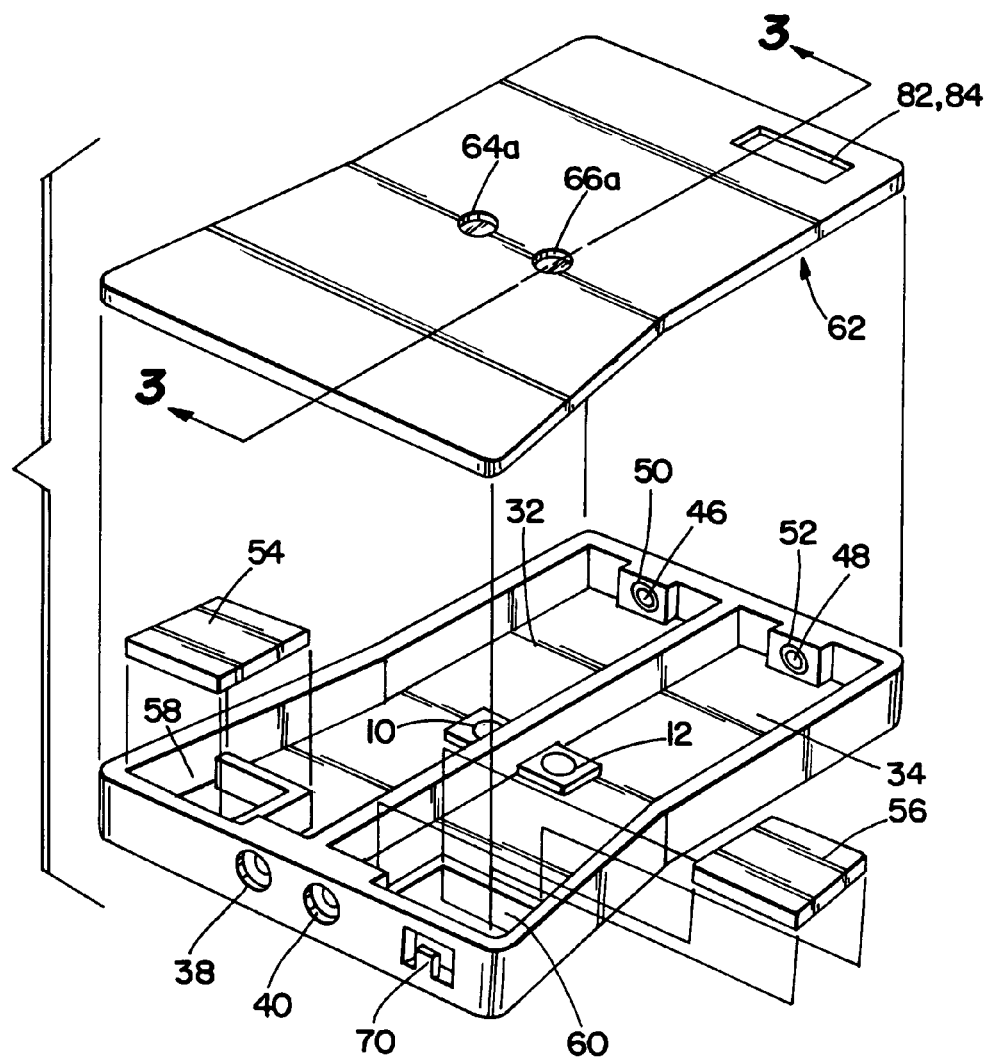
FIG. 2 is an exploded perspective view of a disposable sensor according to an embodiment of the present invention.

The present invention is a disposable sensor comprising a sensing element 10, a means for interfacing 20 the disposable sensor with a gas analysis device, and a housing 30.

The sensing element 10 responds in some quantifiable way to the concentration of an analyte or analytes in the gaseous sample. For instance, in one embodiment, the sensing element is a sol-gel matrix that encapsulates cytochrome-c, which reacts with gaseous NO to produce an optically quantifiable change in the sensing element. Such a sensing element is described in more detail in U.S. Ser. No. 10/334,625. Other potential sensing elements for analysis of NO include other bioactive materials encapsulated within a sol-gel, such as hemoglobin(3+ or 2+ or $O_2$), myoglobin(3+, 2+ or $O_2$), other heme-binding proteins, porphyrin group-containing proteins, heme group-containing proteins, dye-labeled porphyrin group-containing proteins, dye-labeled heme group-containing proteins, and fragments thereof. These materials could be configured to respond in an optically quantifiable manner, or could be configured to respond by a different transduction mechanism, such as electrical impedance or surface acoustic waves. Other suitable sensing materials include organics, inorganics or synthetics that would respond to the analyte in a quantifiable manner.

Many other sensing methods could be used to detect clinically relevant analytes that are present in exhaled breath. These include electrical (impedance, conductance, or resistive)), chemical (electrochemical, spectrophotometric including absorbance, transmission, scattering, reflectance and fluorescence) and acoustic (surface acoustic wave). For example, electrochemistry could be use to detect a wide variety of relevant analytes including hydrogen, nitric oxide, carbon monoxide, provided that the electrochemical sensing element could be inexpensive enough to be practical for a disposable sensor, and also provided that the clinically-required measurement specifications could be met. The disposable sensor could be configured to detect one or more analytes in the exhaled breath. Whenever this patent refers to measurement or analysis of an analyte, such a reference also includes measurement or analysis of more than one analyte.

The sensing element 10 typically has at least two parts: one or more sensing materials (such as cytochrome-c), and a substrate (such as a sol-gel matrix). The sensing material is the molecule that reacts or responds in a quantifiable way to the gas sample or gas sample in the housing 30 surrounding it. The substrate is the carrier or base for the sensing element. It might be (i) a liquid that can hold the bioactive sensing compound in suspension, emulsion or dissolved, or (ii) a polymer or glass that immobilizes the sensing compound. Suitable immobilization agents include sol-gels, sol-gel hybrids (ormosils), Polyvinyl alcohol, Polymethylmethacrylate, polydimethylsiloxane, glass, or related compounds. Any polymer or immobilization agent that allows reaction of the sensing compound with the gas can be used.

As noted above, the sensing element 10 responds in a quantifiable way to the analyte or analytes of interest. Thus, in the embodiment described above, when the cytochrome-c complex adds a NO adduct, its spectral peak red-shifts in the blue region of the spectrum, and this change can be detected. For purposes of this patent, optically-quantifiable characteristics include but are not limited to color, absorption, transmission, reflectance, scattering, luminescence, fluorescence, or phosphorescence.

Figure 8:
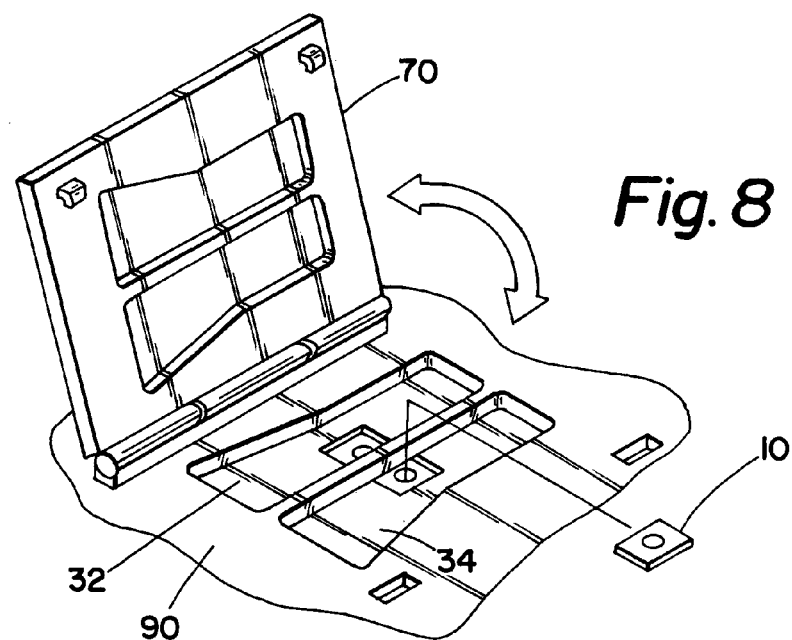
FIG. 8 is a perspective view of a disposable sensing element and a gas analysis device with a sensor housing and door according to an embodiment of the present invention.
Figure 9A:
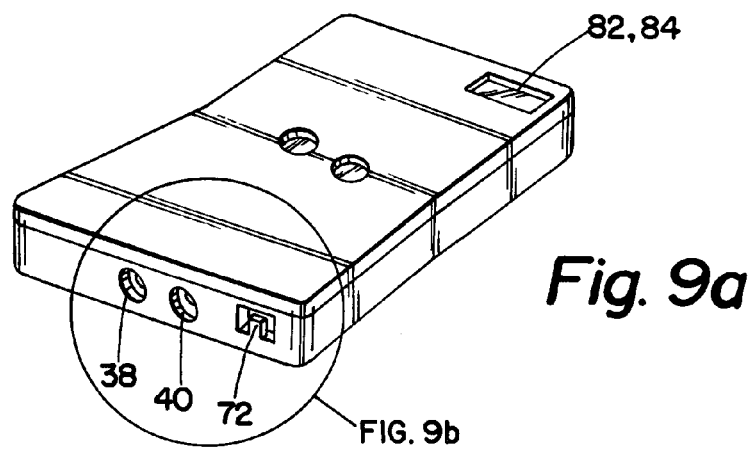
FIGS. 9a–9c depict the operation of a non-reuse tab in a disposable sensor according to an embodiment of the present invention.
Figure 9B:
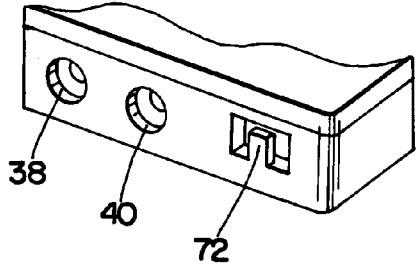
Figure 9C:
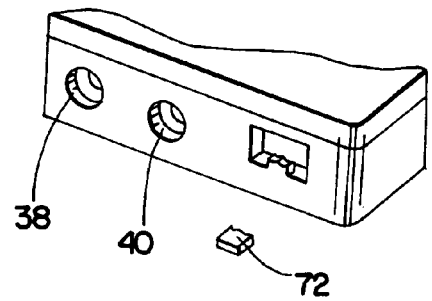
Figure 10:
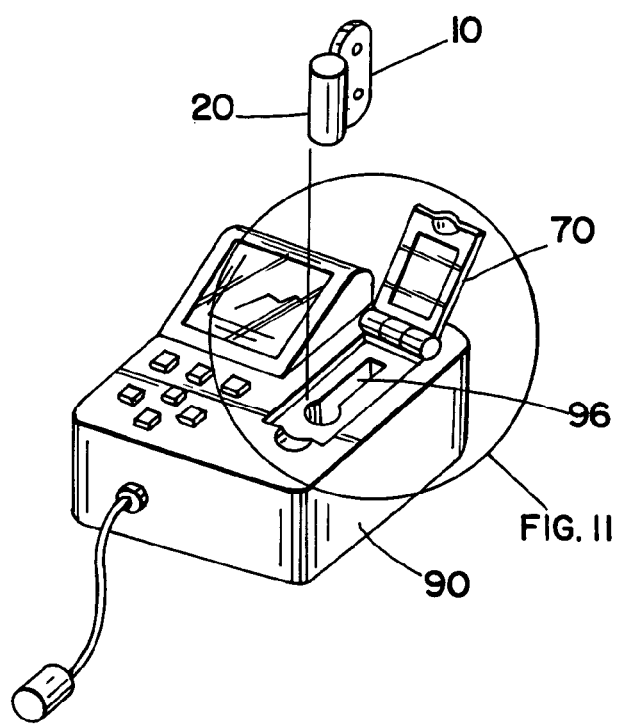
FIG. 10 depicts a disposable sensor with interface means according to an embodiment of the present invention being installed into a gas analysis device.
Figure 11:
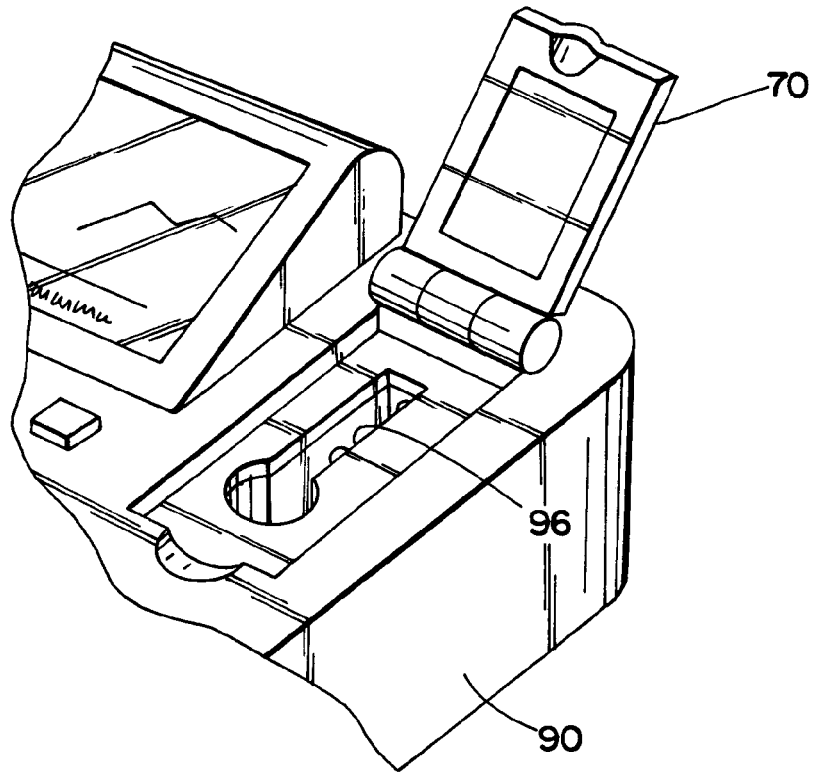
FIG. 11 is a close up of the sensor and sensor recess as depicted in FIG. 10.

The disposable sensor has an interface means 20 for interfacing with an appropriate gas analysis device, such as the device described in U.S. Ser. No. 10/334,625. See FIGS. 10 and 11. This interface means 20 ensures that the sensor is properly aligned and installed into the device. This means 20 could take the form of a slot or recess 96 in the device, and the sensor would be shaped appropriately to fit into the slot 96. See FIGS. 10 and 11. The slot 96 would be configured to allow alignment of the transparent portion 64a, 64b, 66a, 66b of the sensor housing 30 with the optical transducers that would be used to measure the change in the optical characteristics of the sensor. See FIGS. 10 and 11. The slot and the sensor could be configured into a shape that would prevent incorrect insertion of the sensor such as an "L" shape or a triangle, or the shape depicted in FIGS. 10 and 11. The slot and sensor could have a detent and tab combination positioned such that the sensor is locked into place when it is correctly positioned within the device. Alternatively the gas analysis device could have a hinged or sliding door 70 that would secure and position the sensor in place when closed. See FIGS. 8, 10 and 11. The sensor may also have alignment aids to ensure that the sensor is properly installed. These alignment aids may take the form of locating pins and holes, guiding rails, hand stops, precise pockets etc., and these aids may be in either the device or the sensor. Alternatively, a bayonet structure, a screw-on structure, or a peg-structure could be used to secure the sensor to the gas analysis device, so that the optical components are properly aligned.

Figure 13:
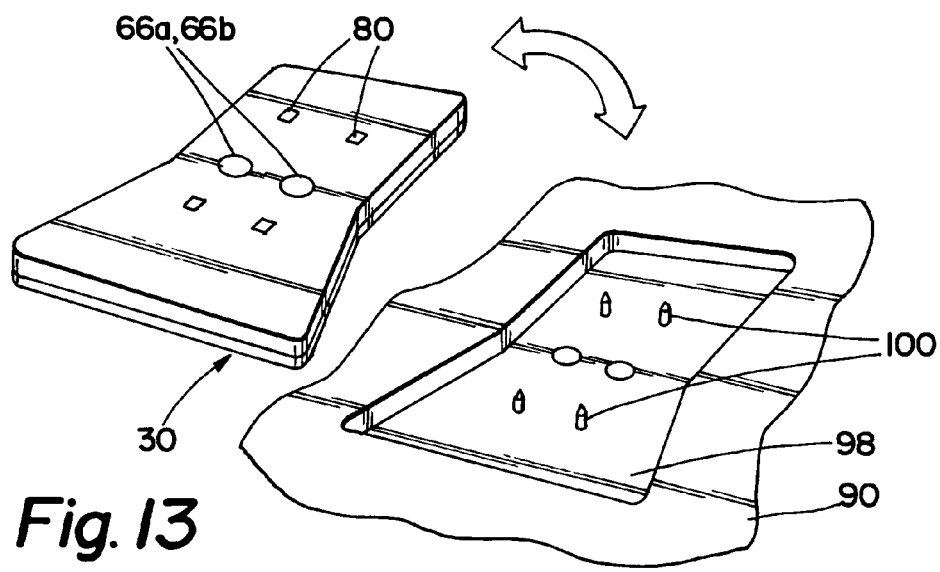
FIG. 13 depicts a sensor with electrical pads, according to an embodiment of the present invention, as it is being installed into the housing recess of a gas analysis device.
Figure 14:
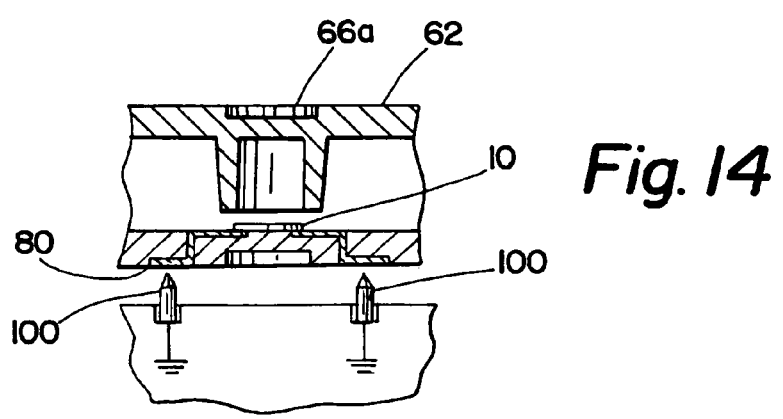
FIG. 14 is a close-up cross section of the sensing element, electrical pads, and electrical pins of the sensor and gas analysis device shown in FIG. 13.

The sensing element 10 could be mounted on a sensing element holder 36 within the housing 30, and the housing 30 creates at least one chamber or cell 32 to contain the gaseous sample. See FIGS. 2, 3, 4, 6, 7, 8, and 12. The housing 30 also protects the sensing element, from the time that it is manufactured until the time that is used, from exposure to the analyte or other gasses that may interfere with its performance. In one embodiment the housing will have a transparent portion (window) 64a, 64b, 66a, 66b to facilitate detection of the optical changes to the sensing element 10. If the sensor uses a different transduction mechanism, the housing would have the appropriate detector interface mechanism for that transduction mechanism. For example, if the sensing element were electrochemical, the sensor may have electrical leads or pads 80 that would allow the analyzer to measure the current or charge produced by the sensor. See FIGS. 13 and 14. These leads or pad would contact electrical pins or electrodes 100 in the gas analysis device 90. See FIGS. 13 and 14. Electrical contact would be made when the housing 30 is correctly placed within the housing recess 98 of the gas analysis device 90. See FIGS. 13 and 14.

The housing 30 will also have an inlet port or ports 38, 40 for entry of the gaseous sample and an outlet port or ports 46, 48 for exit of the gas. See FIGS. 2, 3, 6, 7, 9a–9c, and 12. If necessary to protect the sensing elements from ambient gasses, these ports could have protective covers 42, 44, 50, 52 that would be punctured, removed or otherwise opened when the sensor was ready to perform a measurement. See FIGS. 2, 3, 6, 7, 9a–9c, and 12. The inlet and outlet tubes 92, 94 of the device would be inserted into the ports to allow the device to flow a gaseous sample through the sensor housing, and if the ports had protective covers these tubes could be made from stainless steel and be sharpened to facilitate puncturing of the covers. See FIG. 3. The protective cover could be made of a relatively impermeable membrane such as polymer-foil laminate material or polymer film to prevent the diffusion of interfering gasses into the housing. If protection from the environment was not required to maintain the performance of the sensor the housing could be substantially built into the analyzer rather than part of the disposable. See FIG. 8. The housing 30 may also have a cover 62 that in conjunction with sealed inlet and outlet ports seals and protects the sensor and creates an enclosed, controllable environment within the gas cell or cells. See FIG. 2. In another embodiment, it is also possible to have a protective seal in place of the housing cover that is removed prior to insertion if the change in the sensor housing due to a change in environment is slow enough not to cause interference with the measurement. The sensor also may have means for sealing the ports 38, 40, 46, 48 after opening so that the sensor is ready for use.

The housing 30 will typically be small, but obviously it must be large enough to hold the sensing element 10, and should be sized so that it can be easily inserted into the gas analysis device 90. In one embodiment, where the exhaled gas is trapped in the housing for the measurement, the sensor housing 30 must be large enough to hold a sufficient quantity of exhaled gas so that the concentration of the analyte does not decrease appreciably during the measurement process. If the volume is too small the sensing element 10 could use a significant portion of the analyte reducing the amplitude of the sensing element's response and, in turn, reducing the sensitivity of device. For a sol-gel encapsulated cytochrome-c based NO analyzer with approximately 25 to 50 µL of a 0.03 mM cytochrome-c solution, the volume of the measurement sample inside the housing should be larger than approximately 3 milliliters. If the exhaled gas is allowed to flow past the sensing element 10 during the measurement procedure, then the size of the housing 30 is not limited in this fashion. All or part of the housing need not be disposable and the inlet and outlet ports can attach to the disposable or non-disposable parts of the housing.

The housing 30 could be made of many different materials, such as polycarbonate, acrylic, fluorocarbon polymer, polypropylene, polystyrene, glass, or metal and should be inert to the analyte that is being measured. To reduce the likelihood that fingerprint smudges will impair optical analysis, the transparent portions of the housing (windows) 64a, 64b, 66a, 66b could be placed within recesses 68, 69, thereby placing the windows out of the reach of the user's fingers. Other protective embodiments include a window lining that is removable prior to insertion or is self-removed upon insertion, covering the window with ribs/mesh or building up the wall around the windows to prevent smudges or other optical interferences.

The sensor may also have a use limitation means 82 for ensuring that it is not re-used more than a certain number of times, or after removal from the gas analysis device, or after an expiration date. See FIGS. 2, 9a–9c. There are several different mechanisms that could serve as a use limitation means 82. For instance, the use limitation means 82 could be an information storage device containing a code, such as an integrated circuit (such as an EEPROM or RF tag) or a magnetic strip or bar code. The gas analysis device could read that code, and prevent or discourage re-use after the code has been used a certain number of times (such as once, or 30 times). Or the code could indicate an expiration date, and the gas analysis device could prevent or discourage use of any sensor installed after its installation date. The use limitation means 82 could also be mechanical or electrical, such as a tab 72 that is sensed mechanically prior to use and then broken or perforated during the measurement process. See FIGS. 9a–9c. Or the use limitation means 82 could be a single-use electrical fuse that is burned during use, or a mechanism that senses the force required to puncture the inlet or outlet protective covers of the housing, or a system that interfaces with either the inlet or outlet ports and then draws and measures a vacuum or pressure leaks inside the housing, thereby identifying sensors that have been already used once. Finally, the use limitations means 82 could include a device for obtaining a spectral measurement to monitor a baseline level that is consistent with a reaction with nitric oxide.

Another feature of the present invention is the ability to provide pre-calibrated disposable sensors to the user, thereby eliminating the requirement that the analyzer be periodically calibrated by the user. This provides a significant advantage to the user because calibration typically requires a cumbersome and difficult procedure whereby certified gases are injected into the device in order to determine calibration coefficients that are used in the calculation of the analyte concentration during a test. With disposable sensors the calibration coefficients can be determined at the factory for each sensor. Depending on the repeatability of the manufacturing process, calibration coefficients could be determined for a batch of sensors or, if necessary, for each individual sensor. The calibration coefficients or code corresponding to a look-up table could then be printed on the sensor packaging so that they can be entered into the analyzer and used for the calculation of the analyte concentration. There are many alternative methods to get the correct calibration coefficients into the analyzer: A batch of sensors could be provided with a calibration code that, when entered into the device, could be used as an index in a lookup table to find the appropriate coefficients. The calibration coefficients could be stored in an EEPROM, RF tag or magnetic strip in the sensor that could be read by the gas analysis device 90 prior to use. See FIG. 2. The sensor could have a calibration resistor or capacitor (or combination) whose value or values would be read by the gas analysis device 90 and used to calculate or look up the coefficients. The analyzer could read a bar code printed on the sensor and use that code to look up coefficients. Or the sensor could have an optical code such as a precise aperture that is read by the analyzer and then converted to calibration coefficient. It is also possible that the device will take an initial measurement of the sensor prior to breath introduction and this will be used to calibrate the device. For purposes of this patent, "calibration information" 84 includes but is not limited to any of the foregoing methods of providing calibration data to the gas analysis device 90 or user. See FIGS. 1, 2.

Sample Conditioning

Depending on the precise nature of the sensing element, the sensor housing could contain a sample conditioning unit or units 54, 56 that filter out unwanted substances from the exhaled breath or other gaseous sample. See FIGS. 2, 3. These sample conditioning units could fit into the sample conditioning unit recesses 58, 60 in the housing 30. See FIGS. 2, 3, 6, 7, 12. For example, if the sensor element 10 responds to or is damaged by the moisture present in the breath, the sensor housing could contain a desiccant such as zeolite to remove water vapor from the sample. Other "gettering" or filtering materials could be used to remove interferents from the sample stream. For example, activated charcoal or silica gels could be used to remove alcohols or other polar molecules, potassium permanganate in combination with charcoal could be used to remove NO and other oxides of nitrogen and zeolites could be used to remove a variety of gasses based on their molecular size. The sample conditioning units 54, 56 could also be used to maintain a storage environment for the sensing element. If, for example, the sensing element required a certain concentration of water vapor to be present for it either to function correctly or to maintain its activity over its shelf life, the sample conditioning units 54, 56 could include "art sorb" (a material designed to maintain a fixed humidity over a wide range of environmental conditions), a saturated salt solution that maintains a fixed humidity, or a desiccant to remove water vapor from the interior of the housing. If equilibration with the environment is required, Nafion, or equivalent, tubing could be incorporated into the device to equilibrate with room humidity and temperature. When separate sensing elements are used to measure different analytes, different sample conditioning units 54, 56 could be used for each analyte.

Differential Measurement

The sensor may also have a system or systems for ensuring that the integrity of the measurement is not compromised by "noise" or other extraneous signals. A common approach to reducing the amount of noise in a measurement is to take a differential measurement. In its simplest implementation this technique requires two channels, one that responds to both the measurement of interest and the noise or interference and one channel that responds primarily to the source of noise. In other, more complicated implementations the signal of interest is reconstructed via a mathematical manipulation of two or more channels. For example, if the two channels respond to the noise in a similar manner but the reference channel has a different gain, the reference channel could be scaled prior to subtraction to better cancel the noise signal. This concept can be extrapolated such that one or both of the channels can be mathematically transformed by linear, nonlinear, time dependent and time varying functions to remove noise from the measurement. There are many common accepted mathematical techniques to determine the transformation required to separate signal from the noise.

Many techniques can be used to create a two-channel system, with one channel that is responsive to noise and the concentration of the analyte and a separate channel that is primarily responsive to only noise. In the simplest embodiment, one channel could contain the sensing element in its path while the second channel does not. In this configuration the channel without the sensing element would respond to noise caused by variations in the light output or changes in ambient conditions while the channel with the sensing element would respond to the same "common mode" noise as well as the changes caused by the analyte. In order to extract the signal of interest from the noise either the ratio of the two signals could be measured or the signals could be scaled appropriately and then subtracted.

If there are additional sources of noise, beyond the noise due to variations of the light intensity reaching the sensing element, more complex differential measurement schemes could be implemented. For example, two sensing elements 10, 12 could be used, one in each of the cells 32, 34, or both in the same cell 32, where one element has been treated so that it does not respond to the analyte but does respond to other interfering signals. See FIGS. 2 and 7. Examples of such treatment include chemically, thermally, electrically or photonically denaturing the sensing material, coating the sensing element with a material that is not permeable to the analyte such as Nafion, removing the cytochrome c from the sensing element, modifying the cytochrome-c structure to make it unresponsive to the analyte or using a sensing material that responds similarly to interferents (such as a porphyrin ring or similar protein) but not to the analyte. Alternatively, two similar sensing elements could be used, but the gas sample could be split into two separate gas cells 32, 34, where the analyte is selectively removed from one cell so that both channels respond to potential interfering gases in addition to other noise sources (like light intensity variations) while one channel responds to the analyte as well. Nitric oxide could be removed by using a potassium permanganate filter to react the NO to produce NOx and charcoal to remove the NOx, or a zeolite could be used to trap the NO. In this configuration one gas cell may have a sample conditioning unit 54 or both cells may have different sample conditioners.

Diffusion Port

Figure 12:
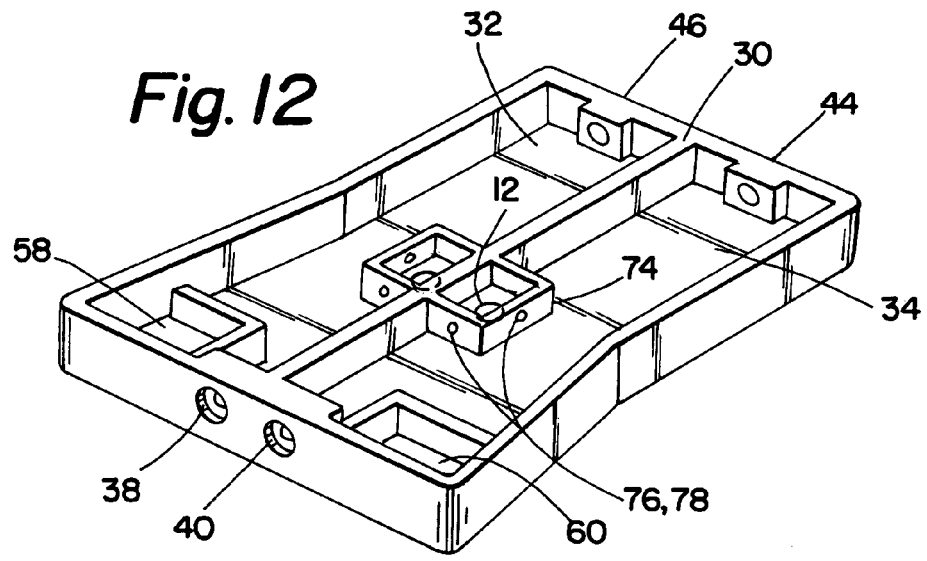
FIG. 12 is a perspective view of a sensor with diffusion ports, with its housing cover removed, according to an embodiment of the present invention.

Since many of the proposed sensor elements require a chemical reaction to take place to sense the analyte, and since chemical reactions are inherently temperature sensitive, it may be advantageous to have a diffusion port or ports 76, 78 between the sensing element and the exhaled gas sample in order to limit the rate of reaction to a known value. The diffusion characteristics of the analyte, while temperature dependent, can be significantly less sensitive to temperature than the rate of the chemical reaction. Therefore the diffusion port will decrease the sensitivity of the analyzer to temperature variations. A diffusion port will also make the device less sensitive to other factors that affect the rate of reaction such as process variables, formulation variations, changes in substrate and others. In effect the diffusion port would act as a well controlled "rate limiting step" in the transduction mechanism reducing the variability in the performance of the device. The diffusion ports 76, 78 can take the form apertures in a sensing element barrier 74 which shields the sensing element 12 from the bulk of the sample inside the gas cell 32, 34, as shown in FIG. 12.

Packaging

Figure 5A:
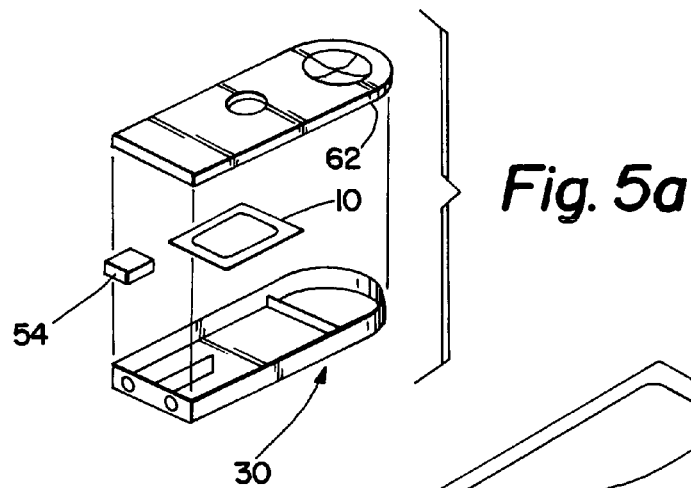
FIGS. 5a, 5b, and 5c depicts the sequence of assembling and packaging a disposable sensor according to an embodiment of the present invention.
Figure 5B:
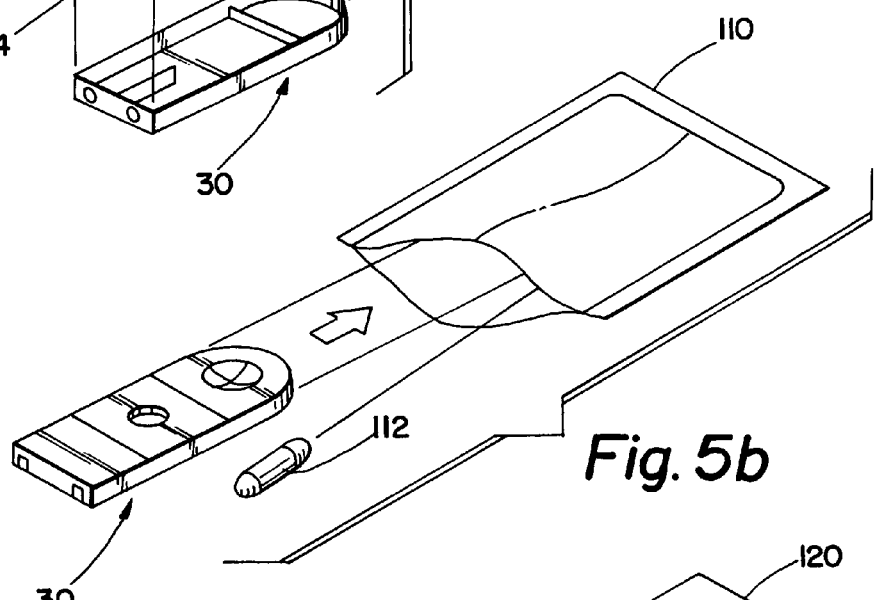
Figure 5C:
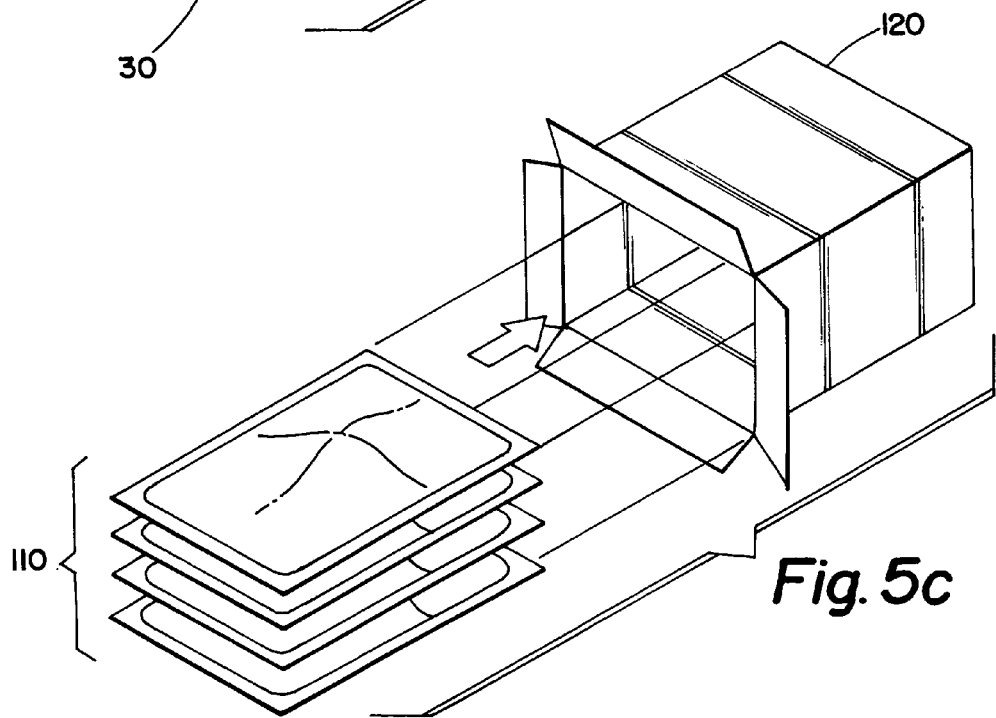

Certain types of sensing elements need to be stored in precisely controlled environments to maintain their sensitivity to the analyte at the desired level during storage. For example cytochrome-c encapsulated in a sol gel matrix has different sensitivity to NO depending on the level of ambient water vapor present. For this type of sensor it is desirable to store the sensor at a fixed water vapor concentration so that sensitivity to NO is well characterized when the sensor is used. The water vapor concentration may also play a role in maintaining the sensitivity of the sensor over time and could be important in determining the shelf-life of the sensor. It might also be necessary to protect the sensor from the ambient levels of the analyte. In order to maintain this specific environment, as could be done inside the housing using the sample conditioning units, a storage compound 112, such as a desiccant and/or a saturated salt solution may need to be placed in the storage pouch 110 for the sensor. See FIGS. 5a, 5b, and 5c. The storage compound (desiccants and/or salt solutions) may need to be stored with each individual sensor or with groups of sensors in their primary packaging 110, particularly if the pouch is re-sealable. The primary packaging can then be in the secondary packaging 120. See FIGS. 5a, 5b, and 5c.

Depending on the use, the sensing element will need to have certain performance characteristics. For instance, in the embodiment in which cytochrome-c in a sol-gel is used to measure NO for managing asthma, the sensing element may have a measurement range of 0–200 ppb, with a minimum detection limit of 5 ppb, and a resolution of 2.5 ppb.

In operation, the user would insert the disposable sensor into the device, and then use a breath-sampling system to transport the breath to the sensor housing. Breath analysis would then occur one or more times, and afterwards, the user would remove and dispose of the sensor. The sensor may be used to perform more than one measurement. Subsequently, upon next use, the user would install a new sensor. No tools would typically be required to install or remove the disposable sensor.

The sensor of the present invention is disposable, but that does not mean that it must necessarily be disposed of after a single use. Instead, for purposes of the present patent, "disposable" merely denotes that the sensor should not be used more than thirty times, and that it should not be re-used after removal from the device.

One skilled in the art will appreciate that the present invention can be practiced by other than the preferred embodiments, which are presented for purposes of illustration and not of limitation.

We claim:

1. A method of measuring the concentration of nitric oxide in a range of 5 to 200 ppb in a gas sample of exhaled breath, said method comprising:
    providing a first disposable sensor, said first sensor comprising a sensing element comprising cytochrome-c in a sol-gel, wherein said sensing element undergoes a change in the presence of 5 to 200 ppb of nitric oxide;
    loading said first sensor into a gas analysis device;
    measuring the concentration of nitric oxide in an exhaled breath sample using said first disposable sensor and said gas analysis device;
    removing said first disposable sensor from said device; and installing a second disposable sensor into said device, said second disposable sensor likewise comprising a sensing element comprising cyrochrome-c and a sol-gel and undergoing a change in the presence of 5 to 200 ppb of nitric oxide.

2. The method according to claim 1, wherein said first and second disposable sensors are within disposable housings.

3. The method according to claim 1, wherein said change is a change in an optically quantifiable characteristic.

4. The method according to claim 1, further comprising employing means for ensuring that extraneous signals do not interfere with measurement of nitric oxide.

5. The method according to claim 4, wherein said means for ensuring that extraneous signals do not interfere with measurement comprises two separate channels for analysis of the gas, wherein one of said channels is used for reference analysis.

6. The method according to claim 4, wherein said means for ensuring that extraneous signals do not interfere with measurement comprises using two separate sensing elements for analysis of the gas, wherein one of said elements is used for reference analysis.

7. The method according to claim 1, additionally comprising conditioning the gas sample before measurement.

8. The method according to claim 1, wherein said first disposable sensor uses calibration information associated with said sensor.

9. A device for quantifying the concentration of nitric oxide in a range of 5 to 200 ppb in a gaseous sample of exhaled breath, said device comprising:
a disposable sensing element comprising cytocbrome-c in a sol-gel and having a nitric oxide measurement range of 5 to 200 ppb; and
an interface means for interfacing said disposable sensing element with the remainder of said device.

10. The device of claim 9, wherein said interface means comprises a means for aligning an optical window in said disposable sensing element with an optical transducer on said device.

11. The device of claim 9, wherein said disposable sensing element generates an electrical signal and said interface means comprises a means to align electrical contacts on said disposable sensing element with electrical contacts on the remainder of said device.

12. The sensor according to claim 9, wherein said interface means comprises a slot in said device and a guide in said disposable sensing element.

13. The device of claim 9, further comprising two gas cells, one containing said disposable sensing element and the other containing a second said sensing element and means for selectively removing said nitric oxide from exposure to said second sensing element.

14. A kit for determining the concentration of nitric oxide in a sample of exhaled breath in which said nitric oxide is present in an amount ranging from 5 to 200 ppb, said kit comprising:
a plurality of disposable sensors, wherein said sensors comprise cytochrome-c in a sol-gel having a nitric oxide response range of 5 to 200 ppb;
a gas analysis device for use with said sensors, said device comprising means for receiving exhaled breath and converting said response to a measurable signal.

* * * * *